(12) United States Patent
Boamfa et al.

(10) Patent No.: US 12,148,152 B2
(45) Date of Patent: Nov. 19, 2024

(54) CORRELATED IMAGE ANALYSIS FOR 3D BIOPSY

(71) Applicant: KONINKLIJKE PHILIPS N.V., Eindhoven (NL)

(72) Inventors: Marius Iosif Boamfa, Veldhoven (NL); Pieter Jan Van Der Zaag, Waalre (NL); Rowan Cornelis Van Hoogenhuizen, Eindhoven (NL); Michel Jozef Agnes Asselman, Helmond (NL); Roland Cornelis Martinus Vulders, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 308 days.

(21) Appl. No.: 17/437,351

(22) PCT Filed: Mar. 9, 2020

(86) PCT No.: PCT/EP2020/056193
§ 371 (c)(1),
(2) Date: Sep. 8, 2021

(87) PCT Pub. No.: WO2020/182720
PCT Pub. Date: Sep. 17, 2020

(65) Prior Publication Data
US 2022/0180510 A1   Jun. 9, 2022

(30) Foreign Application Priority Data
Mar. 13, 2019   (EP) ..................... 19162476

(51) Int. Cl.
| G06T 7/00 | (2017.01) |
| G06V 10/80 | (2022.01) |
| G06V 20/69 | (2022.01) |
| G16H 30/40 | (2018.01) |

(52) U.S. Cl.
CPC .......... G06T 7/0012 (2013.01); G06V 10/803 (2022.01); G06V 20/695 (2022.01);
(Continued)

(58) Field of Classification Search
CPC ..................... G06T 7/0012; G06T 7/00; G06T 2207/10064; G06T 2207/30024;
(Continued)

(56) References Cited

U.S. PATENT DOCUMENTS

| 8,131,476 B2 | 3/2012 | Cline |
| 8,421,033 B2 | 4/2013 | Kishima |

(Continued)

FOREIGN PATENT DOCUMENTS

| JP | 2017522022 A | 8/2017 |
| JP | 2018503906 A | 2/2018 |

OTHER PUBLICATIONS

PCT International Search Report, International application No. PCT/EP2020/056193, May 28, 2020.
(Continued)

*Primary Examiner* — Tuan H Nguyen
(74) *Attorney, Agent, or Firm* — Sherry Austin (57) ABSTRACT

The present invention relates to image analysis of pathology images. In order to improve reliability in image analysis of pathology images, a method is provided for providing support in identifying at least one feature of a tissue sample in a microscopic image. The method comprises the steps of providing a first image of a first microscopy 5 modality representing an area of the tissue sample, providing a second image of a second microscopy modality representing the said area of the tissue sample, generating a first high intensity image by applying a first high intensity filter to the first image or a first low intensity image by applying a first low intensity filter to the first image to obtain first informa-
(Continued)

tion of the at least one feature, generating a second high intensity image by applying 10 a second high intensity filter to the second image or a second low intensity image by applying a second low intensity filter to the second image to obtain second information of the at least one feature, calculating a correlation of an image pair comprising one of the first high intensity image and the first low intensity image and one of the second high intensity image and the second low intensity image for correlating the first information and the second 15 information of the at least one feature, and outputting the calculated correlation for providing support in identifying the at least one feature of the tissue sample.

19 Claims, 4 Drawing Sheets (52) U.S. Cl.
CPC .......... *G06V 20/698* (2022.01); *G16H 30/40* (2018.01); *G06T 2207/10056* (2013.01); *G06T 2207/10064* (2013.01); *G06T 2207/30024* (2013.01)

(58) Field of Classification Search
CPC .......... G06T 2207/10056; G16H 30/40; G06V 20/695; G06V 20/698; G06V 20/69
See application file for complete search history.

(56) References Cited

U.S. PATENT DOCUMENTS

| | | | |
|---|---|---|---|
| 9,224,031 B2 * | 12/2015 | Glensbjerg | ........... G02B 21/125 |
| 9,310,302 B2 | 4/2016 | Garsha | |
| 2007/0139764 A1 | 6/2007 | Vodyanoy | |
| 2017/0309021 A1 * | 10/2017 | Barnes | ................. G06T 7/0012 |
| 2019/0213736 A1 | 7/2019 | Varekamp | |

OTHER PUBLICATIONS

Yigitsoy M. et al., "Hierarchical Patch-Based Co-Registration of Differently Stained Histopathology Slides", Progress in Biomedical Optics and Imaging, SPIE—International Society for Optical Engineering, Bellingham, WA, US, vol. 10140, Mar. 1, 2017, pp. 1014009-1014009, XP060086715.
Uttam S. et al., "Early Prediction of Cancer Progression by Depth-Resolved Nanoscale Maps of Nuclear Architecture from Unstained Tissue Specimens", Cancer Research, Nov. 15, 2015; 75(22): 4718-4727.
Zhu H. et al., "Cost-Effective and Compact Wide-Field Fluorescent Imaging on a Cell-Phone", Lab Chip., Jan. 2011, 11(2): 315-322.
Wood B.R. et al., "Resonance Raman Microscopy in Combination with Partial Dark-Field Microscopy Lights Up a New Path in Malaria Diagnosis", Analyst, 2009, 134, 1119-1125.
"FDA Allows Marketing of First Whole Slide Imaging System for Digital Pathology", FDA News Release, Apr. 12, 2017.
Pantanowitz L. et al., "Digital Pathology", 2017.
Pantanowitz L. et al., "Twenty Years of Digital pathology: An Overview of the Road travelled, What is on the Horizon, and the Emergence of Vendor-Neutral Archives", 2018 Journal of Pathology Informatics, vol. 1, No. 40, pp. 1-12, 2018.
Can A. et al., "Multi-Modal Imaging of Histological Tissue Sections", 2008 5th IEEE International Symposium on Biomedical Imaging, IEEE , 2008, pp. 288-291.

* cited by examiner

CORRELATED IMAGE ANALYSIS FOR 3D BIOPSY

CROSS-REFERENCE TO RELATED APPLICATIONS

This patent application claims the priority benefit under 35 U.S.C. § 371 of International Patent Application no. PCT/EP2020/056193, filed Mar. 9, 2020, which claims the benefit of European Patent Application No. EP19162476.6, filed on Mar. 13, 2019. These applications are hereby incorporated by reference herein in their entirety.

FIELD OF THE INVENTION

The present invention relates to image analysis of pathology images. In particular, the present invention relates to a method, a data processing apparatus, and a system for providing support in identifying at least one feature of a tissue sample in a microscopic image, as well as a computer program element and a computer readable medium.

BACKGROUND OF THE INVENTION

Pathologic examination of a tissue sample, e.g. a human tissue sample or a biopsy, may involve the identification of certain features of interest in the tissue sample. For example, in a three-dimensional biopsy analysis it is required to detect a gradual increase in the density alternation of cells nuclear architecture or sample inner morphology. Various microscopy modalities have been developed for providing volumetric or two-dimensional microscopic imaging of e.g. optical absorption, reflection, or scattering contrasts in biological tissues.

U.S. Pat. No. 9,224,301 B2 describes image analysis of dark-field images. Particles to be discriminated are identified in fluorescence analysis and can be removed in the analysis of at least one dark-field image. However, the features of interest may be incorrectly identified due to e.g. image artefacts or simple signal intensity variations across the tissue sample.

SUMMARY OF THE INVENTION

There may be a need to improve reliability in image analysis of pathology images.

The object of the present invention is solved by the subject-matter of the independent claims, wherein further embodiments are incorporated in the dependent claims. It should be noted that the following described aspects of the invention apply also for the method, the data processing apparatus, the system, the computer program element, and the computer readable medium.

A first aspect of the present invention relates to a method for providing support in identifying at least one feature of a tissue sample in a microscopic image. The method comprises the steps of providing a first image of a first microscopy modality representing an area of the tissue sample, providing a second image of a second microscopy modality representing the said area of the tissue sample, generating a first high intensity image by applying a first high intensity filter to the first image or a first low intensity image by applying a first low intensity filter to the first image to obtain first information of the at least one feature, generating a second high intensity image by applying a second high intensity filter to the second image or a second low intensity image by applying a second low intensity filter to the second image to obtain second information of the at least one feature, calculating a correlation of an image pair comprising one of the first high intensity image and the first low intensity image and one of the second high intensity image and the second low intensity image for correlating the first information and the second information of the at least one feature, and outputting the calculated correlation for providing support in identifying the at least one feature of the tissue sample.

In other words, in order to enhance the detection of a predefined feature of a tissue sample, e.g. a nuclei, it is proposed to correlate detected information of the predefined feature in an image of a first one microscopy modality with detected information of the same feature in a second one microscopy modality; that is, the feature information that comes from the second modality is used as a complementary feature information of the first modality.

The tissue sample may be obtained from a sample selected from e.g. a liver sample, a kidney sample, a muscle sample, a brain sample, a lung sample, a skin sample, a thymus sample, a spleen sample, a gastrointestinal tract sample, a pancreas sample, a prostate sample, a breast sample, or a thyroid gland sample. The tissue samples may originate from e.g. a human sample, or from an animal such as a mouse sample, a rat sample, a monkey sample, or a dog sample.

The first and second microscopy modalities may include various light microscopy modalities that allow investigation of biological structures. The microscopy modalities may include fluorescence microscopy imaging, such as epi-fluorescence microscopy, total internal reflection fluorescence (TIRF) microscopy, confocal microscopy, or multiphoton excitation microscopy. The microscopy modalities may also include absorption-based microscopy modalities, such as bright-field microscopy, stimulated emission microscopy, photoacoustic microscopy, or optical projection tomography (OPT). Additionally, microscopy modalities may include scattering-based microscopy, such as dark-field microscopy and optical coherence tomography (OCT). As will be explained hereafter and particularly with respect to the exemplary embodiment in FIG. 1 and FIGS. 2A to 2C, the first and second microscopy modalities may be dark-field and fluorescence microscopy imaging.

A high or low intensity filter is applied to the first and second image to extract the information of the feature. For example, the presence of certain cells can be detected by specific staining of their cellular membranes by, for instance, fluorescently labeled antibodies and using fluorescence microscopy. One can also extract the information on cell nuclei using a nuclear stain and a fluorescence microscope image. A high intensity filter may be applied to the fluorescence microscope image to identify pixels representative for regions where the sample density is high and there is little or no scattering, indicating an area with many cell nuclei. For example, to extract the information of tubuli in a fluorescence microscope image, a low intensity filter may be applied to the fluorescence microscope image to identify pixels representative for regions where the sample density is low and there is a lot of scattering, indicating an area around the tubuli in the tissue sample. As a further example, to extract the information of cell nuclei in a dark-field microscope image, a low intensity filter may be applied to the dark-field image to identify pixels representative for regions where the sample density is high and there is little or no scattering, indicating an area with a lot of cell nuclei. To extract the information of tubuli in a dark-field microscope image, a high intensity filter may be applied to identify pixels representative for regions where the sample density is low and there is a lot of scattering, indicating an area around the tubuli in the tissue sample. The high or low intensity filter may be a threshold filter. Thresholding identifies pixels with intensity values in particular ranges. In an example, thresholding with a high intensity filter may identify pixels above a particular threshold value. In another example, thresholding with a low intensity filter may identify pixels below a particular threshold value. Various thresholding techniques may be employed, including, but not limited to, global thresholding, local thresholding, Histogram shape-based thresholding, clustering-based thresholding, and object attribute-based thresholding. Global thresholding applies the same thresholds to every pixel in the entire image. Local thresholding may be applied in the situation where the background itself in the image varies in brightness. Color images, e.g. fluorescence images, can also be thresholded. One approach is to designate a separate threshold for each of the RGB components of the image and then combine them with an AND operation.

It is also noted that the term "generating a high intensity or low intensity image" refers to obtaining high intensity or low intensity image data. It is not required to display the high intensity or low intensity image.

The correlation may use a correlation coefficient as a measure of similarity between two images in the image pair for each location. The image pair may include one of the first high intensity image and the first low intensity image and one of the second high intensity image and the second low intensity image for correlating the first information and the second information of the at least one feature. In other words, the image pair may include at least one of the following combinations: i) the first high intensity image and the second high intensity image, ii) the first high intensity image and the second low intensity image, iii) the first low intensity image and the second high intensity image, and iv) the first low intensity image and the second low intensity image. The image combination in the image pair is dependent on the first and second microscopy modalities and the feature to be detected. For example, to extract the information of cell nuclei, the image pair may comprise a high intensity fluorescence microscope image and a low intensity dark-field microscope image, as will be explained in FIG. 1 and FIGS. 2A to 2C, since the contrast enhancement works differently in these two modalities. On the other hand, to extract the information of cell nuclei, the image pair may comprise a high intensity fluorescence microscope image and a high intensity bright-field image, since the contrast enhancement works similarly in these two modalities. The result will be maximum for locations where both images have correspondence. These locations are representative for the pixels of the feature to be identified in the first and the second image. As will be explained hereafter and particularly with respect to the exemplary embodiment in FIG. 1, the correlation may be based on a Boolean operation or other more complicated methods. The identification of the feature may thus be performed, e.g. manually or automatically with an algorithm, based on the correlation coefficient.

As the first image of the first microscopy modality and the second image of the second microscopy modality may not have the same image artefacts, or the same signal intensity variations across the tissue sample, the correlation may eliminate or reduce their negative effects. Thus, the identification process may be more reliable. This may be beneficial for a machine-based identification process using image segmentation and feature extraction methods. Thus, these method steps may be carried out in the image conditioning stage for the next stage of image segmentation and feature extraction. In other words, these method steps may manipulate a microscope image to eliminate or reduce the negative effect of image artefacts and/or signal variations across the tissue sample such that it meets the requirements of the next stage for further image processing. Thus, the features of interest may have a higher chance to be correctly identified.

According to an embodiment of the present invention, the first microscopy modality and the second microscopy modality are different modalities selected from at least one of the following: fluorescence microscopy imaging, dark-field microscopy imaging, and bright-field microscopy imaging.

According to an embodiment of the present invention, the first microscopy modality is fluorescence microscopy imaging and the second microscopy modality is dark-field microscopy imaging.

The fluorescence microscopy imaging may allow the visualization of fluorescent marked structures such as cell stained through fluorescent labeled antibodies on their cell membranes or through staining of the cell nucleus using a nuclear staining or a so-called intercalating dye. The dark-field microscopy imaging may allow the identification of boundaries and internal cavities. Combining two imaging modalities may thus give extra information about the tissue. They may lead, for instance, to a better assessment of where the tubuli are within the tissue being imaged.

According to an embodiment of the present invention, the image pair comprises the first high intensity image and the second low intensity image or the first low intensity image and the second high intensity image.

This may be beneficial for the situations where the contrast enhancement of two microscopy modalities works differently. In an example, an absorption-based imaging modality, e.g. bright-field, is combined with a scattering-based imaging modality, e.g. dark-field or OCT. In another example, a fluorescence imaging modality is combined with a scattering-based imaging modality. For example, a high intensity dark-field image and a low intensity fluorescence image are representative for regions where the sample density is low and there is a lot of scattering, e.g. around the ducts or tubuli in the sample. On the other hand, a low intensity dark-field image and a high intensity fluorescence image are representative for regions where the sample density is high and there is little or no scattering, indicating an area with many cell nuclei, indicative for abnormal tissue activity.

According to an embodiment of the present disclosure, the correlation is calculated based on a Boolean operation.

For example, a pixel-by-pixel Boolean multiplication may be performed to obtain a cross-correlation matrix. Other more complicated methods may also be used, which will be explained hereafter and particularly with respect to the exemplary embodiment in FIG. 1.

A second aspect of the present invention relates to a system for providing support in identifying at least one feature of a tissue sample in a microscopic image. The system comprises a data processing apparatus described above and below and a display. The display is configured to display at least one of the first and second images and the calculated correlation between the first extracted information and the second extracted information of the at least one feature output from the data processing apparatus.

A third aspect of the invention relates to a data processing apparatus for providing support in identifying at least one feature of a tissue sample in a microscopic image. The data processing apparatus comprises an input unit, an information extraction unit, a correlation unit, and an output unit. The input unit is configured to receive a first image of a first microscopy modality representing an area of the tissue sample and a second image of a second microscopy modality representing the said area of the tissue sample. The information extraction unit is configured to generate a first high intensity image by applying a first high intensity filter to the first image or a first low intensity image by applying a first low intensity filter to the first image to obtain first information of the at least one feature, and to generate a second high intensity image by applying a second high intensity filter to the second image or a second low intensity image by applying a second low intensity filter to the second image to obtain second information of the at least one feature. The correlation unit is configured to calculate a correlation of an image pair comprising one of the first high intensity image and the first low intensity image and one of the second high intensity image and the second low intensity image for correlating the first information and second information of the at least one feature. The output unit is configured to output the calculated correlation for providing support in identifying the at least one feature of the tissue sample.

For the data processing apparatus the same explanations apply as for the method as outlined above. Thus, the data processing apparatus may provide image conditioning to remove image artefacts and signal variations across the tissue sample in a microscope image, thereby making the microscope image suitable and reliable for further processing, e.g. image segmentation and feature extraction, in machine-based image processing methods.

The term "unit" as used herein may refer to, be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality.

According to an embodiment of the present invention, the data processing apparatus comprises a feature identification unit. The feature identification unit is configured to identify the at least one feature based on at least one of the first and second images and the calculated correlation.

In other words, the data processing apparatus may perform the feature identification after conditioning. As the microscope image after conditioning is more reliable, the chance of correct identification of the features of interest in a tissue sample may be increased.

According to an embodiment of the present invention, the first microscopy modality and the second microscopy modality are different modalities selected from at least one of the following: fluorescence microscopy imaging, dark-field microscopy imaging, and bright-field microscopy imaging.

According to an embodiment of the present invention, the first microscopy modality is fluorescence microscopy imaging and the second microscopy modality is dark-field microscopy imaging.

Accordingly, boundaries and internal cavities can be visualized with the dark-field microscopy imaging and fluorescent marked structures (e.g. cancer cells) can be visualized with the fluorescence microscopy imaging. In this way, both structures can be combined in one three-dimensional rendering.

According to an embodiment of the present invention, the image pair comprises the first high intensity image and the second low intensity image or the first low intensity image and the second high intensity image.

According to an embodiment of the present invention, the correlation unit is configured to calculate the correlation based on a Boolean operation.

A fourth aspect of the present invention relates to a computer program element for instructing an apparatus described above and below, which, when being executed by a processing unit, is adapted to perform the method steps described above and below.

A fifth aspect of the present invention relates to a computer readable medium having stored the program element.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
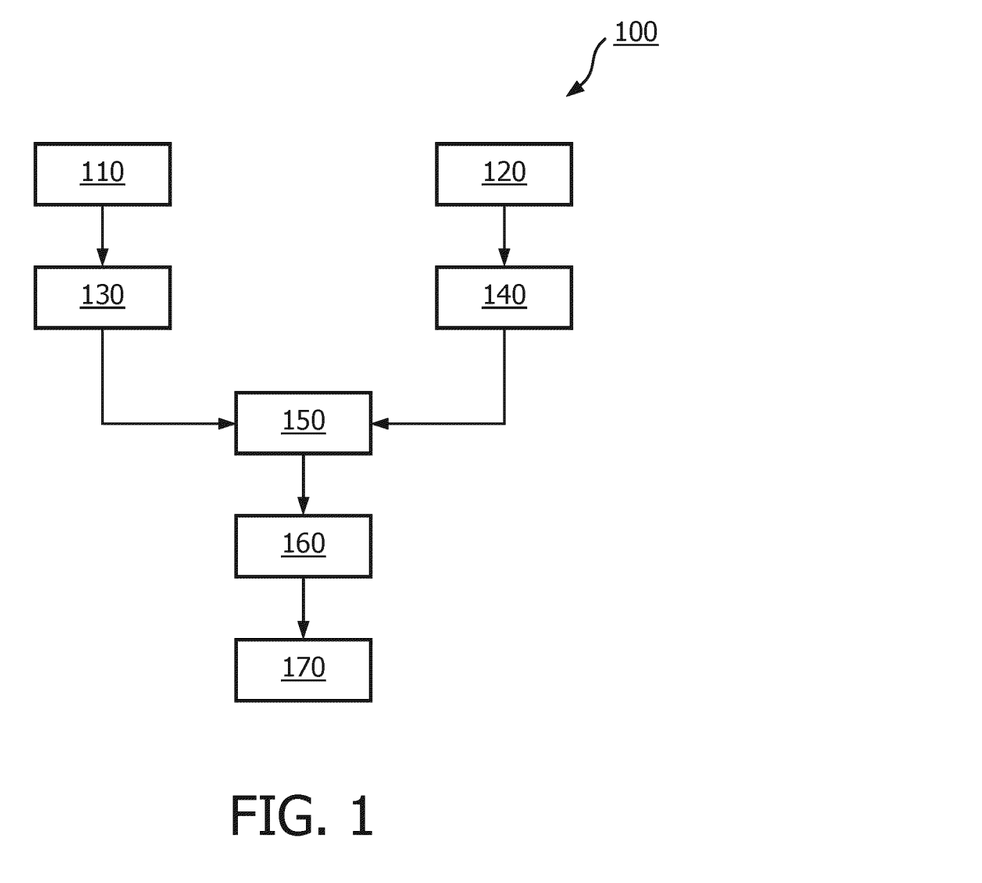
FIG. 1 shows a flow diagram of a method for providing support in identifying at least one feature of a tissue sample in a microscopic image according to some embodiments of the present disclosure.
Figure 2A:
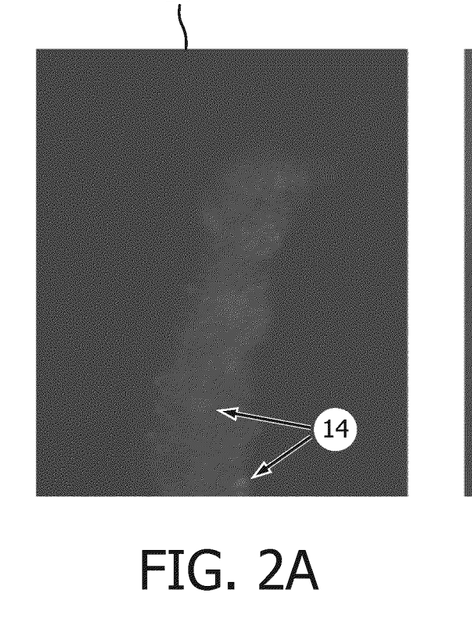
FIG. 2A shows a fluorescence microscope image of a region of a rat liver according to some embodiments of the present disclosure.
Figure 2B:
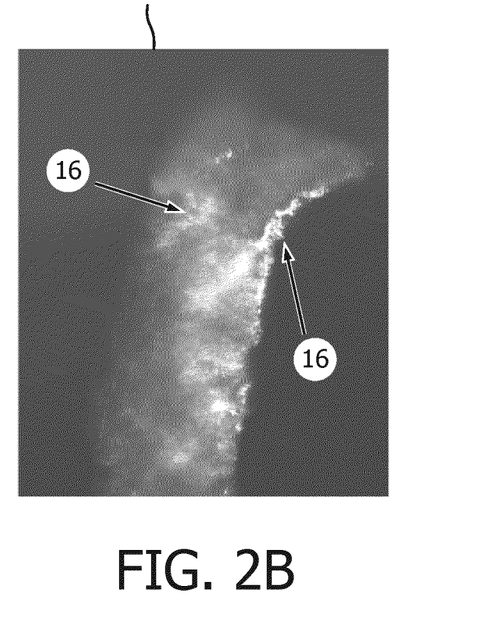
FIG. 2B shows a dark-field microscope image of the same region of the rat liver according to some embodiments of the present disclosure.
Figure 2C:
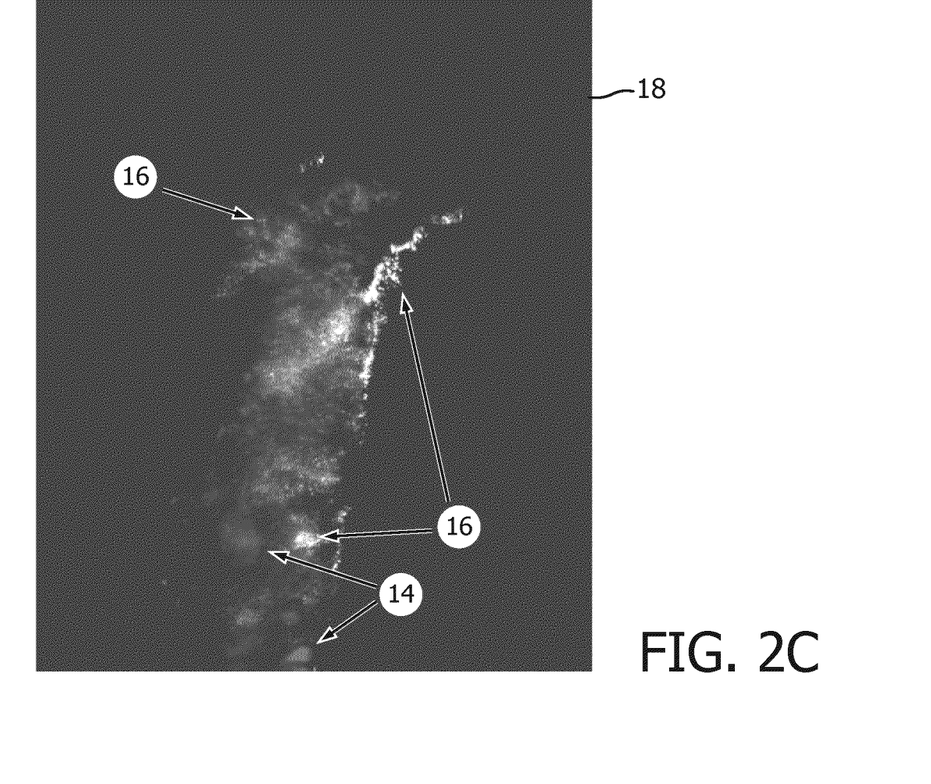
FIG. 2C shows an overlay of the filtered fluorescence microscope image and the filtered dark-field microscope image of the same region of the rat liver according to some embodiments of the present disclosure.

FIG. 1 illustrates a flow diagram of a method 100 for providing support in identifying at least one feature 14, 16 (see FIGS. 2A-2C and FIGS. 3A-3C) of a tissue sample in a microscopic image according to some embodiments of the present disclosure. FIGS. 2A to 2C show a set of rat liver images for illustrating the method steps according to an exemplary embodiment of the present disclosure. In particular, a fluorescence microscope image of a region of the rat liver acquired under 620 nm laser excitation is shown in FIG. 2A. In this example, a SiR DNA nuclear dye (Spirochrome, Switzerland) is used. This is a far-red, fluorogenic, cell permeable and highly specific probe for DNA (with no specificity for tumor vs. normal cells). A dark-field microscope image of the same region of the rat liver acquired under 840 nm laser illumination is shown in FIG. 2B. An overlay of a filtered fluorescence microscope image and a filtered dark-field microscope image is shown in FIG. 2C.

In step 110, a first image 10 of a first microscopy modality representing an area of the tissue sample is provided. For example, the first image 10 may be the fluorescence microscope image as illustrated in FIG. 2A and the first microscopy modality may be fluorescence microscopy imaging.

In step 120, a second image 12 of a second microscopy modality representing the said area of the tissue sample is provided. For example, the second image 12 may be the dark-field microscope image as illustrated in FIG. 2B and the second microscopy modality may be dark-field microscope imaging.

In step 130, a first high intensity image (not shown) is generated by applying a first high intensity filter to the first image 10. Alternatively, a first low intensity image (not shown) is generated by applying a first low intensity filter to the first image 10 to obtain first information of the at least one feature 14, 16. It is noted that the first high or low intensity image refers to first high or low intensity image data. It is thus not required to display the first high or low intensity image.

The selection of the first high intensity filter or the first low intensity filter is dependent on the feature to be identified. For example, the high intensity regions 14 in the fluorescence microscope image, i.e. the first image 10, in FIG. 2A are representative for regions where the sample density is high and there is a no or less scattering, indicating an area with many cell nuclei. Thus, a high intensity filter may be applied to the fluorescence microscope image in FIG. 2A to obtain the information of cell nuclei. On the other hand, a low intensity filter may be applied to the fluorescence microscope image in FIG. 2A to identify regions where the sample density is low and there is a lot of scattering, indicating an area around ducts or tubuli.

A high intensity filter may be defined as $$g(x, y) = \begin{cases} f(x, y), & \text{if } f(x, y) \geq T \\ 0, & \text{otherwise} \end{cases}$$

where T is the threshold value, x, y are the coordinates of the first or second image f(x,y), and g(x,y) is the threshold image after applying the high intensity filter.

A low intensity filter may be defined as $$g(x, y) = \begin{cases} f(x, y), & \text{if } f(x, y) \leq T \\ 0, & \text{otherwise} \end{cases}$$

The threshold value T may be a manual threshold defined by a user. Alternatively, the threshold value may be determined from histograms by an automated method. For global thresholding, the threshold value T is identical for every pixels in the entire images. For local thresholding, the threshold T varies across the entire image, and may thus be defined as T(x,y).

In step 140, a second high intensity image (not shown) is generated by applying a second high intensity filter to the second image 12. Alternatively, a second low intensity image (not shown) is generated by applying a second low intensity filter to the second image to obtain second information of the at least one feature 14, 16. It is also noted that the second high or low intensity image refers to second high or low intensity image data. It is also not required to display the second high or low intensity image.

The selection of the second high intensity filter or the second low intensity filter is also dependent on the feature to be identified. For example, the high intensity regions 16 in the dark-field microscope image, i.e. the second image 12, in FIG. 2B are representative for regions where the sample density is low and there is a lot of scattering, indicating areas around ducts or tubuli. Thus, a high intensity filter may be applied to the dark-field microscope image in FIG. 2B to obtain the information of ducts or tubuli. On the other hand, a low intensity filter may be applied to the dark-field microscope image in FIG. 2B to identify regions where the sample density is high and there is less or no scattering, indicating an area with a lot of cell nuclei.

In step 150, a correlation of an image pair is calculated. The image pair comprises one of the first high intensity image and the first low intensity image and one of the second high intensity image and the second low intensity image for correlating the first information and the second information of the at least one feature.

In an example, the at least one feature to be identified include cell nuclei, a correlation of a high intensity fluorescence microscope image and a low intensity dark-field microscope image may be calculated, since both images are representative for regions where the sample density is high and there is no or less scattering, indicating an area with many cell nuclei.

In another example, the at least one feature to be identified include ducts and nuclei, a correlation of a low intensity fluorescence microscope image and a high intensity dark-field microscope image may be calculated, since both images are representative for regions where the sample density is low and there is a lot of scattering, indicating an area with ducts and tubuli.

The above-mentioned two examples may also be combined to generate an overlay, such that both features, i.e. cell nuclei and ducts or tubuli, can be identified in an overlay image 18 as illustrated in FIG. 2C. In this example, the correlation is calculated based on a Boolean operation. A binary image is used, in which each pixel can only have one of two values to indicate whether it is part of the at least one feature to be identified or not. The correlation is calculated by multiplexing the binary images of the image pair, although more advanced correlation methods may be used. In the overlay image 18, it is easy to see the regions 14 where the sample density is high and there is no or less scattering, indicating an area with many cell nuclei, and regions 16 where the sample density is low and there is a lot of scattering, indicating an area with ducts or tubuli.

Alternative to the Boolean operation, the correlation may also be calculated using more complicated methods, such as $$r = \sum_m \sum_n \frac{(A_{mn} - \overline{A})(B_{mn} - \overline{B})}{\sqrt{\left(\Sigma_m \Sigma_n (A_{mn} - \overline{A})^2\right)\left(\Sigma_m \Sigma_n (B_{mn} - \overline{B})^2\right)}}$$

where r is the correlation coefficient, m, n are the coordinates of the first or second image $A_{mn}$ and $B_{mn}$, $\overline{A}$ is the mean of $A_{mn}$ and $\overline{B}$ is the mean of $B_{mn}$.

In step 160, the calculated correlation is outputted for providing support in identifying the at least one feature of the tissue sample.

Figure 3A:
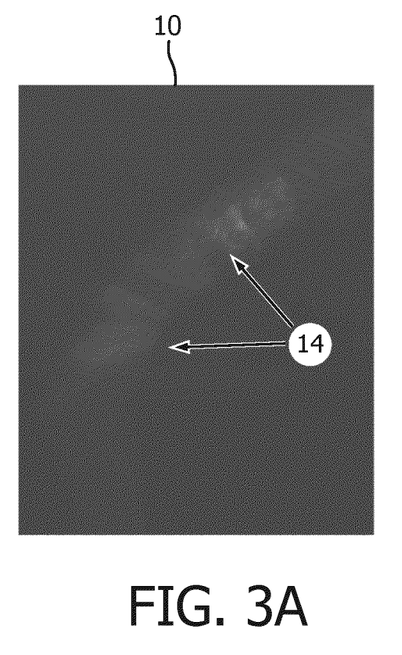
FIG. 3A shows a fluorescence microscope image of a region of a human prostate according to some embodiments of the present disclosure.
Figure 3B:
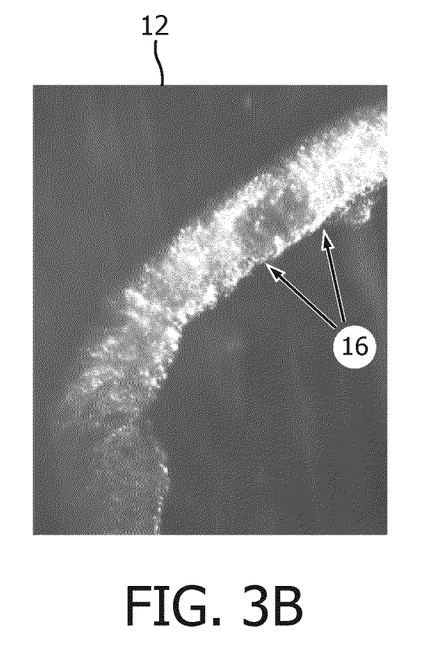
FIG. 3B shows a dark-field microscope image of the same region of the human prostate according to some embodiments of the present disclosure.
Figure 3C:
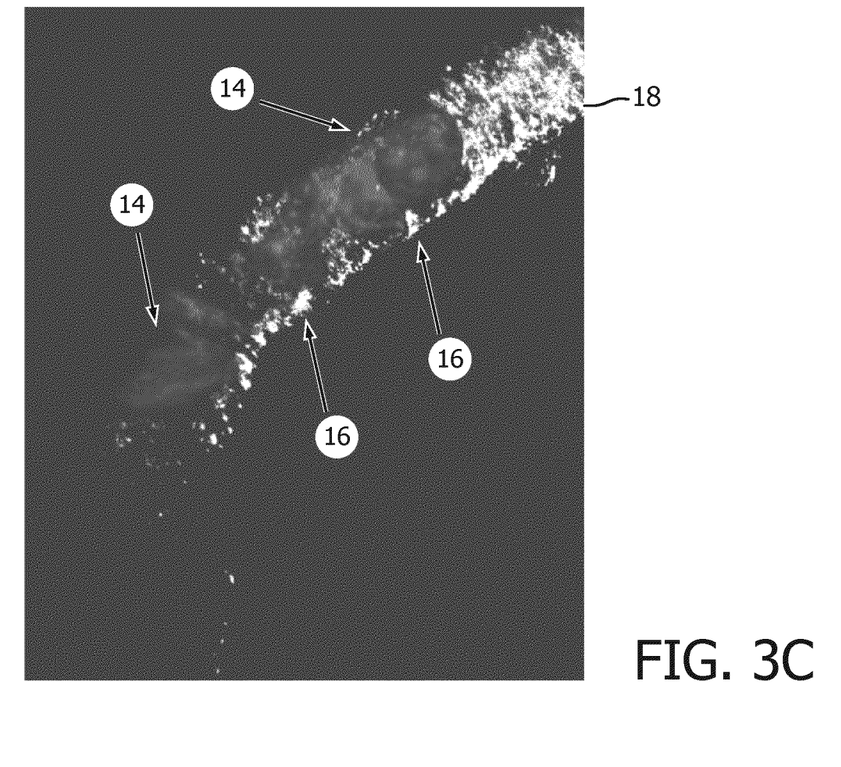
FIG. 3C shows an overlay of the filtered fluorescence microscope image and the filtered dark-field microscope image of the same region of the human prostate according to some embodiments of the present disclosure.

FIGS. 3A to 3C show a set of human prostate images for illustrating the method steps according to an exemplary embodiment of the present disclosure. A fluorescence microscope image 10 of a region of the human prostate acquired under 620 nm laser excitation is shown in FIG. 3A. A SiR DNA nuclear dye (Spirochrome, Switzerland) is used which is a far-red, fluorogenic, cell permeable and highly specific probe for DNA (with no specificity for tumor vs. normal cells). In particular, a dark-field microscope image 12 of the same region of the rat liver acquired under 530 nm laser illumination is shown in FIG. 3B. An overlay image 18 of a filtered fluorescence microscope image and a filtered dark-field microscope image is shown in FIG. 3C with a similar analysis performed in FIGS. 2A to 2C.

Correlating information of a feature obtained from two different microscopy modalities may solve the problem of image artefacts, or simple signal intensity variations across the sample, thereby rending the identification process of the feature reliable. This may be beneficial for a machine-based method for providing a reliable and fast tissue analysis.

Optionally, in step 170, the at least one feature is identified based on at least one of the first and second images and the calculated correlation.

In an example, this identification step may be performed manually by a user.

In another example, the identification step may be performed automatically based on image segmentation and feature extraction methods. For example, the calculated correlation, e.g. a resulting cross-correlation matrix, can serve as a pixel-by-pixel weighting function, which can be multiplied to the first image or the second image to identify a single feature, such as ducts and tubuli or cell nuclei, or to the sum of the two images for identifying both features. Image segmentation and feature extraction may be performed on the at least one of the first weighted and second weighted images.

Figure 4:
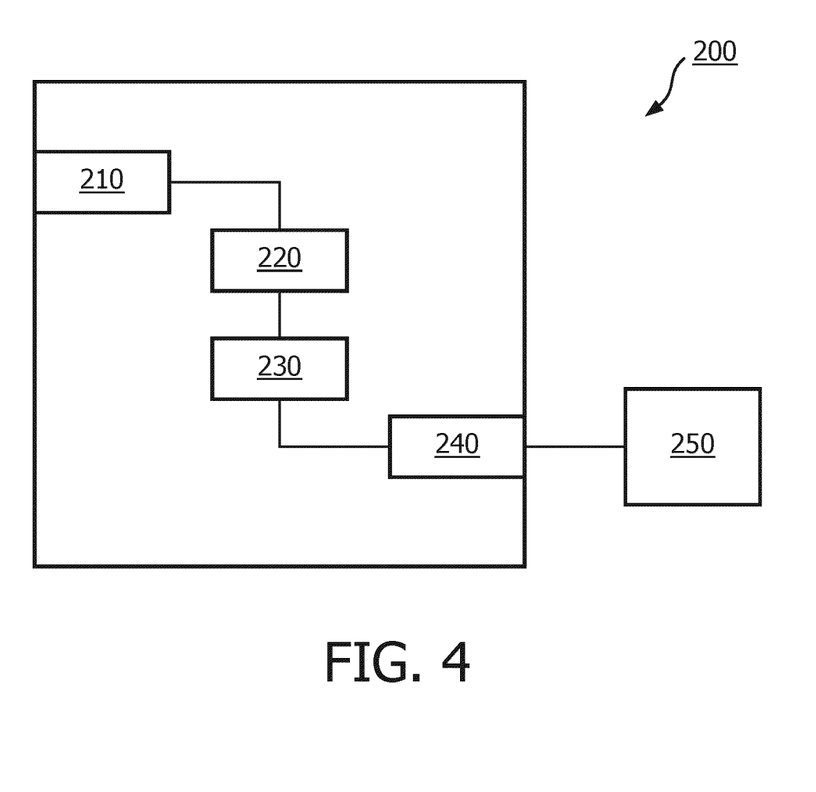
FIG. 4 shows a data processing apparatus for providing support in identifying at least one feature of a tissue sample in a microscopic image according to some embodiments of the present disclosure.

FIG. 4 shows a data processing apparatus 200 providing support in identifying at least one feature of a tissue sample in a microscopic image according to some embodiments of the present disclosure. The data processing apparatus 200 comprises an input unit 210, an information extraction unit 220, a correlation unit 230, and an output unit 240, which may be part of, or include an ASIC, an electronic circuit, a processor (shared, dedicated, or group) and/or memory (shared, dedicated, or group) that execute one or more software or firmware programs, a combinational logical circuit, and/or other suitable components that provide the described functionality.

The input unit 210 is configured to receive a first image of a first microscopy modality representing an area of the tissue sample and a second image of a second microscopy modality representing the said area of the tissue sample.

The information extraction unit 220 is configured to generate a first high intensity image by applying a first high intensity filter to the first image or a first low intensity image by applying a first low intensity filter to the first image to obtain first information of the at least one feature, and to generate a second high intensity image by applying a second high intensity filter to the second image or a second low intensity image by applying a second low intensity filter to the second image to obtain second information of the at least one feature. For example, the first microscopy modality and the second microscopy modality are different modalities selected from at least one of the following: fluorescence microscopy imaging, dark-field microscopy imaging, and bright-field microscopy imaging. In an example, the first microscopy modality is fluorescence microscopy imaging and the second microscopy modality is dark-field microscopy imaging.

The correlation unit 230 is configured to calculate a correlation of an image pair comprising one of the first high intensity image and the first low intensity image and one of the second high intensity image and the second low intensity image for correlating the first information and second information of the at least one feature. For example, the image pair comprises the first high intensity image and the second low intensity image or the first low intensity image and the second high intensity image. For example, the correlation unit 206 is configured to calculate the correlation based on a Boolean operation.

The output unit 240 is configured to output the calculated correlation for providing support in identifying the at least one feature of the tissue sample.

Optionally, the data processing apparatus further comprises a feature identification unit 250. The feature identification unit 250 is configured to identify the at least one feature based on at least one of the first and second images and the calculated correlation.

Figure 5:
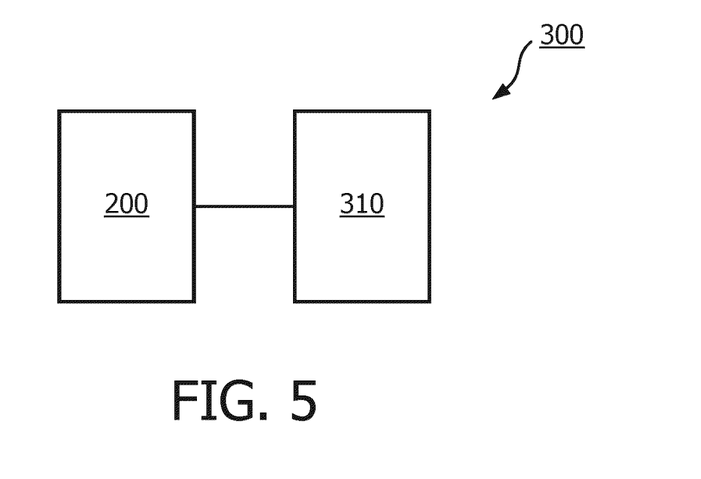
FIG. 5 shows a system for providing support in identifying at least one feature of a tissue sample in a microscopic image according to some embodiments of the present disclosure.

FIG. 5 shows a system 300 for providing support in identifying at least one feature of a tissue sample in a microscopic image according to some embodiments of the present disclosure. The system 300 comprises a data processing apparatus 200 as described above and below and a display 310. The display 310 is configured to display at least one of the first and second images and the calculated correlation between the first extracted information and the second extracted information of the at least one feature output from the data processing apparatus.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method for identifying at least one feature of a tissue sample in a microscopic image, comprising the following steps:
   receiving a first image of a fluorescence microscopy imaging modality representing an area of the tissue sample;
   receiving a second image of a dark field microscopy imaging modality representing the said area of the tissue sample;
   and,
   generating a first high intensity image by applying a first high intensity filter to the first image to obtain first information of the at least one feature;
   generating a second low intensity image by applying a second low intensity filter to the second image to obtain second information of the at least one feature;
   calculating a high-low correlation of the first high intensity image and the second low intensity image for correlating the first information and the second information of the at least one feature;
   providing the high-low calculated correlation for providing support in identifying the at least one feature of the tissue sample;
   or
   generating a first low intensity image by applying a first low intensity filter to the first image to obtain the first information of the at least one feature;
   generating a second high intensity image by applying a second high intensity filter to the second image to obtain the second information of the at least one feature;
   calculating a low-high correlation of the first low intensity image and the second high intensity image for correlating the first information and the second information of the at least one feature;
   providing the low-high calculated correlation for providing support in identifying the at least one feature of the tissue sample.

2. Method according to claim 1, wherein the high-low correlation or low-high correlation is calculated based on a Boolean operation.

3. A non-transitory computer readable medium having stored thereon a computer program that when executed by a processor causes the processor to perform the method steps of claim 1.

4. The method of claim 1, wherein correlating includes obtaining a cross-correlation matrix using a pixel-by-pixel Boolean multiplication.

5. The method of claim 1, wherein the high or low intensity filter is a threshold filter.

6. The method of claim 5, wherein the threshold filter is clustering-based threshold filter.

7. The method of claim 5, wherein the threshold filter is an attribute-based threshold filter.

8. The method of claim 5, wherein the threshold filter is a local threshold filter.

9. The method of claim 5, wherein the threshold filter is a histogram-based threshold filter.

10. A data processing apparatus for providing support in identifying at least one feature of a tissue sample in a microscopic image, comprising:
    an input unit;
    an information extraction unit;
    a correlation unit; and
    an output unit;
    wherein the input unit is configured to receive a first image of a fluorescence microscopy imaging modality representing an area of the tissue sample and a second image of a dark field microscopy imaging modality representing the said area of the tissue sample; and wherein,
    the information extraction unit is configured to generate a first high intensity image by applying a first high intensity filter to the first image to obtain first information of the at least one feature, to generate a second low intensity image by applying a second low intensity filter to the second image to obtain second information of the at least one feature;
    the correlation unit is configured to calculate a high-low correlation of the first high intensity image and the second low intensity image for correlating the first information and second information of the at least one feature;
    the output unit is configured to output the calculated high-low correlation for providing support in identifying the at least one feature of the tissue sample;

or wherein,
the information extraction unit is configured to generate a low intensity image by applying a first low intensity filter to the first image to obtain first information of the at least one feature, to generate a second high intensity image by applying a second high intensity filter to the second image to obtain second information of the at least one feature;
the correlation unit is configured to calculate a low-high correlation of the first low intensity image and the second high intensity image for correlating the first information and second information of the at least one feature,
the output unit is configured to output the calculated low-high correlation for providing support in identifying the at least one feature of the tissue sample.

11. The data processing apparatus according to claim 10, wherein the correlation unit is configured to calculate the high-low correlation or low-high correlation based on a Boolean operation.

12. A system for providing support in identifying at least one feature of a tissue sample in a microscopic image, comprising:
a data processing apparatus according to claim 10; and
a display;
wherein the display is configured to display at least one of the first and second images and the calculated high-low correlation or low-high correlation between the first extracted information and the second extracted information of the at least one feature output from the data processing apparatus.

13. A method for identifying at least one feature of a tissue sample in a microscopic image, comprising the following steps:
receiving a first image of an fluorescence microscopy imaging modality representing an area of the tissue sample;
receiving a second image of a dark field microscopy imaging modality representing the said area of the tissue sample;
and,
generating a first high intensity image by applying a first high intensity filter to the first image to obtain first information of the at least one feature;
generating a second low intensity image by applying a second low intensity filter to the second image to obtain second information of the at least one feature;
correlating the first information and the second information of the at least one feature;
providing the correlation for providing support in identifying the at least one feature of the tissue sample.

14. The method of claim 13, wherein correlating the first information and the second information of the at least one feature includes calculating a correlation of the first low intensity image and the second high intensity image for correlating the first information and the second information of the at least one feature.

15. A non-transitory computer readable medium having stored thereon a computer program that when executed by a processor causes the processor to perform the method steps of claim 13.

16. The non-transitory computer readable medium of claim 15, wherein correlating includes obtaining a cross-correlation matrix using a pixel-by-pixel Boolean multiplication.

17. A method for identifying at least one feature of a tissue sample in a microscopic image, comprising the following steps:
receiving a first image of a fluorescence microscopy imaging modality representing an area of the tissue sample;
receiving a second image of a dark field microscopy imaging modality representing the said area of the tissue sample;
generating a first low intensity image by applying a first low intensity filter to the first image to obtain the first information of the at least one feature;
generating a second high intensity image by applying a second high intensity filter to the second image to obtain the second information of the at least one feature;
correlating the first information and the second information of the at least one feature;
providing the correlation for providing support in identifying the at least one feature of the tissue sample.

18. The method of claim 17, wherein correlating the first information and the second information of the at least one feature includes calculating a correlation of the first low intensity image and the second high intensity image for correlating the first information and the second information of the at least one feature.

19. A non-transitory computer readable medium having stored thereon a computer program that when executed by a processor causes the processor to perform the method steps of claim 17.

* * * * *